United States Patent
Eng et al.

(10) Patent No.: US 7,346,379 B2
(45) Date of Patent: Mar. 18, 2008

(54) ELECTROPHYSIOLOGY CATHETER

(75) Inventors: Michael J. Eng, Shoreview, MN (US); Raju R. Viswanathan, St. Louis, MO (US); Peter R. Werp, St. Louis, MO (US); Ilker Tunay, St. Louis, MO (US); Ashwini K. Pandey, Collinsville, IL (US); Gareth T. Munger, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 11/319,039

(22) Filed: Dec. 27, 2005

(65) Prior Publication Data

US 2006/0278246 A1 Dec. 14, 2006

Related U.S. Application Data

(63) Continuation of application No. 10/443,113, filed on May 21, 2003, now Pat. No. 6,980,843.

(51) Int. Cl.
- *A61B 5/04* (2006.01)
- *A61B 18/14* (2006.01)
- *A61B 19/00* (2006.01)

(52) U.S. Cl. .................. 600/374; 128/899; 606/41; 607/122

(58) Field of Classification Search ............... 600/374; 606/41; 128/899
See application file for complete search history.

(56) References Cited

U.S. PATENT DOCUMENTS

| | | | |
|---|---|---|---|
| 3,674,014 A * | 7/1972 | Tillander | 600/434 |
| 5,429,131 A * | 7/1995 | Scheinman et al. | 600/374 |
| 5,654,864 A | 8/1997 | Ritter et al. | |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |

(Continued)

*Primary Examiner*—Lee S. Cohen
(74) *Attorney, Agent, or Firm*—Harness, Dickey & Pierce, P.L.C.

(57) ABSTRACT

An electrophysiology catheter includes a tube having a proximal end, a distal end, and a lumen therebetween. The tube is preferably comprised of multiple sections of different flexibility, arranged so that the flexibility of the catheter increases from the proximal end to the distal end. There is a first generally hollow electrode member at the distal end. At least one magnetically responsive element is disposed at least partially in the hollow electrode, for orienting the distal end of the catheter with an externally applied magnetic field. Multiple magnets can be distributed over the distal portion of the device. The end electrode can have openings for delivering irrigating fluid, and/or a sleeve can be provided around the tube to create an annular space for the delivering of irrigating fluid. A temperature sensor can be provided to control the operation of the catheter. A localization coil can also be included to sense the position and orientation of the catheter.

37 Claims, 1 Drawing Sheet

U.S. PATENT DOCUMENTS

| | | |
|---|---|---|
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 2001/0038683 A1 | 11/2001 | Ritter et al. |
| 2002/0019644 A1 | 2/2002 | Hastings et al. |
| 2002/0177789 A1 | 11/2002 | Ferry et al. |
| 2004/0006301 A1 | 1/2004 | Sell et al. |
| 2004/0019447 A1 | 1/2004 | Shachar |
| 2004/0064153 A1 | 4/2004 | Creighton, IV et al. |
| 2004/0068173 A1 | 4/2004 | Viswanathan |
| 2004/0096511 A1 | 5/2004 | Harburn et al. |
| 2004/0133130 A1 | 7/2004 | Ferry et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2005/0020911 A1 | 1/2005 | Viswanathan et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2006/0009735 A1 | 1/2006 | Viswanathan et al. |
| 2006/0025679 A1 | 2/2006 | Viswanathan et al. |
| 2006/0036125 A1 | 2/2006 | Viswanathan et al. |
| 2006/0036163 A1 | 2/2006 | Viswanathan |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0093193 A1 | 5/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |

* cited by examiner

ELECTROPHYSIOLOGY CATHETER

This is a continuation of U.S. patent application Ser. No. 10/443,113, filed May 21, 2003, now U.S. Pat. No. 6,980,843, issued Dec. 27, 2005 the disclosure of which is hereby incorporated by reference.

BACKGROUND OF THE INVENTION

This invention relates to electrophysiology catheters, and in particular to a magnetically guidable electrophysiology catheter.

Electrophysiology catheters are elongate medical devices that are introduced into the body and are used for sensing electrical properties of tissues in the body; applying electrical signals to the body for example for cardiac pacing; and/or applying energy to the tissue for ablation. An electrophysiology catheter typically has a proximal end, a distal end, and at least one, and preferably at least two electrodes on its distal end. Recently, electrophysiology catheters have been made with electrodes having openings in their distal ends for passage of normal saline solution which cools the surface tissues to prevent blood clotting. These electrodes can be difficult to navigate into optimal contact with the tissues using conventional mechanical pull wires.

SUMMARY OF THE INVENTION

Electrophysiology catheters in accordance with the principles of this invention of this invention are particularly adapted for magnetic navigation. The electrophysiology catheter comprises a tube having a proximal end, a distal end, and a lumen therebetween. Of course, solid catheters could also be used. The tube is preferably comprised of multiple sections of different flexibility, each section being more flexible than its proximal neighbor, so that the flexibility of the catheter increases from the proximal end to the distal end. A first generally hollow electrode member is located at the distal end of the tube. The first electrode has a generally cylindrical sidewall and a dome-shaped distal end. There is preferably a second electrode spaced proximally from the first electrode, and there may be a plurality of additional ring electrodes proximal to the first electrode. In accordance with the principles of this invention, several magnetically responsive members are spaced along the length of the catheter. Flexible portions of the catheter are disposed between the magnetically responsive elements. Each of the flexible portions can have a different bending stiffness which, by the inverse relationship between bending stiffness and flexibility, defines the flexibility of each flexible portion. Moreover, because the flexible portions can have different flexibilities, the various flexible portions can have different turn radii, which can be optimized for their particular location within the catheter. The distal end portion of the catheter remains flexible to facilitate navigating the catheter within the body.

The magnetically responsive members can be permanent magnets, permeable magnets, electromagnetic coils, or combinations thereof and will hereinafter be referred to as magnet members. Each magnet member is sized and shaped so that it can orient the part of the catheter in which it is included inside the body under the application of a magnetic field from an external source magnet. The magnet member is preferably responsive to a magnetic field of 0.1 T, and more preferably less. The interplay between the strength and orientation of each magnet member and the flexibility and length of each flexible segment allows segments of the catheter to be oriented in a selected direction at the location of each magnet member with the applied magnetic field. Because of the ability to design flexible segments of the catheter for a particular catheter function, the catheter may navigate and advance through delicate structures in the body inaccessible to most other catheters.

One particularly demanding catheter function, electrical mapping and RF ablation therapy for restoration of normal electrical activity in cardiac chambers, requires a catheter which can extend trans-septally through a puncture in the septal wall of the heart from the right side to the left side and touch the anterior right lateral portions of the circumference of the Mitral Valve. Such navigation places particular demands on the catheter because the navigation requires a sharp, 180 degree navigation of the catheter within the narrow confines of the left ventricle. However, the current state of the art provides no such catheter that is easy to navigate around the Mitral Valve.

BRIEF DESCRIPTION OF THE DRAWINGS

The present invention will become more fully understood from the detailed description and the accompanying drawings, wherein.

Corresponding reference numerals indicate corresponding parts throughout the several views of the drawings.

DETAILED DESCRIPTION OF THE INVENTION

The following description of the preferred embodiments is merely exemplary in nature and is in no way intended to limit the invention, its application, or uses.

Figure 1:
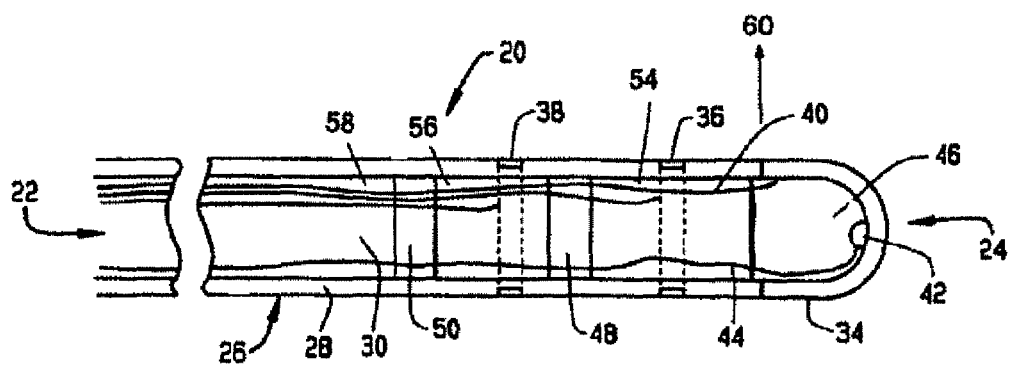
FIG. 1 is a side view of a catheter in accordance with a preferred embodiment of the present invention.

A first embodiment of an electrophysiology catheter constructed according to the principles of this invention is indicated generally as 20 in FIG. 1. The electrophysiology catheter 20 has a proximal end 22 and a distal end 24. The catheter 20 preferably includes a hollow flexible tube 26 with a sidewall 28 and a lumen 30 therethrough. A longitudinal axis 32 extends generally through the lumen 30 in the center of the device. The tube 26 is preferably made from a flexible biocompatible materials such as Pebax™.

As shown in FIG. 1, the catheter 20 can have a dome-shaped end electrode 34 on its distal end, and one or more ring electrodes 36 and 38 which extend around the distal end portion of the tube 26. The ring electrodes may actually have a slit therein to reduce eddy currents when the catheter moves in an applied magnetic field. Lead wires 40 extend proximally from the electrodes 34, 36, and 38 to conduct electrical signals, from the electrodes to a signal processing unit at the proximal end when the catheter is used in sensing and mapping, and to the electrodes 34, 36, and 38 when the catheter is used for ablating tissue. Some of the electrodes can be dedicated for use in recording of electrophysiological electrical activity, others of the electrodes can be used for delivering RF energy to sites within a patient for therapeutic purposes. The electrodes can be disposed over magnetic or nonmagnetic sections of the catheter 20. When placed over a magnetic section of the catheter, the magnet helps apply and control the contact force between the tissue and the electrode, but some or all of the electrodes could be placed over a non-magnetic portion of the catheter as well.

The distal end 24 of the catheter 20 can include a thermocouple or thermistor 42. Leads 44 extend from the thermocouple or thermistor 42 to the proximal end of the catheter. The thermocouple or thermistor 42 allows temperature at the distal end of the catheter to be measured, so that the local effects of the operation of the RF therapy delivery.

As shown in FIG. 1 the catheter 20 has magnetic members 46, 48, and 50 which may be made from or include a permanently magnetized material with a fixed magnetic dipole moment, or a shaped magnetically permeable material that responds magnetically to an applied field so that magnetically induced moments act on the magnetic members 46, 48, and 50. The magnetic members 46, 48, and 50 can be contained within the lumen 30; embedded in the side wall 28 of the catheter 20; or affixed to the side wall 28 in the form of a sleeve around the tube 26. The magnet members 46, 48, and 50 are preferably made from a permanent magnetic material, such as Neodymium-Iron-Boron (Nd—Fe—B) or Samarium-Cobalt, or a permeable magnetic material, such as Hiperco. If any of the magnetic members 46, 48, and 50 is made of a magnetically permeable material, they may be designed in a shape that is inherently flexible, for instance a helically wound coil coaxial with the longitudinal axis of the catheter.

The strongest currently available magnetic material, Neo 53 is well suited for use to form the magnetic members 46, 48, and 50. The use of even stronger magnetic materials for the magnetic members is within the spirit and scope of the present invention.

The magnetic members 46, 48, and 50 can take any size and shape, provided that they provide sufficient response to the applied magnetic field. As shown in FIG. 2, the magnetic members 46 48, and 50 can be sized and shaped to accommodate the leads 40 and 44 within the lumen 30. A second embodiment includes sleeve shaped magnetic members 42' (FIG. 2) which may be disposed anywhere on the outside of the tube 26. In the embodiment shown in FIG. 2, the sleeve shaped magnetic members 46' have an inside diameter of between about 0.008 and 0.15 inches to receive the tube 26, and an outside diameter of between about 0.010 and 0.18 inches; and a length of between about 0.020 and 0.8 inches. The dimensions of the magnet 46' will depend on the size of the tube 26 size, the tube material, catheter function, and the number of leads 40 and 44 in the lumen 30.

Figure 2A:
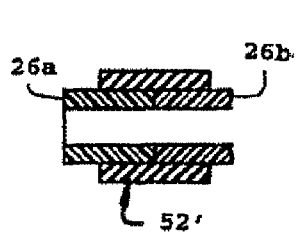
FIG. 2A is a cross sectional view of a portion of a catheter with a first alternate magnetic member in accordance with the principles of this invention.
Figure 2B:
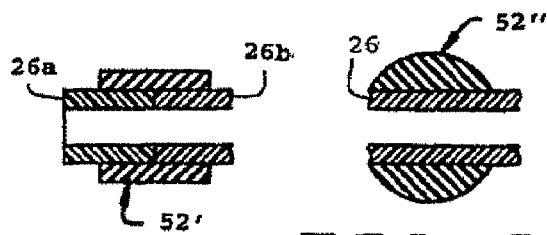
FIG. 2B is a cross sectional view of a portion of a catheter with a second alternate magnetic member in accordance with the principles of this invention.
Figure 2C:
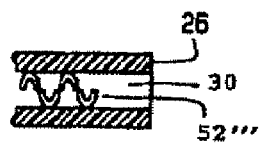
FIG. 2C is a cross sectional view of a portion of a catheter with a third alternate magnetic member in accordance with the principles of this invention.

The sleeve-shaped magnetic members 46' can also be used to aid in connecting tube sections 26a and 26b, as is illustrated in FIG. 2. As show in FIG. 2A, the tube portions 26a and 26b can be flexible segments. Moreover, because the tube portions 26a and 26b can be made separately, from different materials, in difference sizes and configurations. For example, the tube segment 26a and 26b can comprise multiple layers which result in different properties for these sections. Thus, the design of the tube segments 26a and 26b can facilitate adapting the catheter to particular catheter functions and/or to facilitate navigating the catheter to a specific location or configuration for a particular function or procedure.

Alternatively, the magnetic members may have a generally spherical configuration, indicated as 46" in FIG. 2B, with a passage therethrough for mounting the magnet members 46" over the catheter 20. In yet another alternative, the magnetic members may be helically shaped, for example helical member 46''' disposed in the lumen 30, which may be, formed from a magnetic wire.

The various magnetic properties of the magnetic members 42', 42", and 42''', including the identity of the magnetic material, magnetic permeability, magnetic volume, magnetic orientation, and magnetic polarity of each magnetic member 42 can be selected to adapt the responsiveness of the magnetic members to an applied magnetic field.

As to the positions of the magnetic members along the tube 26, in the embodiment shown in FIG. 1, the distal-most magnetic member 46 can be placed within 15 mm of the distal end 24 with satisfactory results. Magnet members 48 and 50 are preferably disposed within 3 to 80 mm of the proximal end of distal-most magnetic member 46. In some embodiments the magnet members are positioned near locations on the catheter 20 where the flexibility of the tube 26 changes (e.g. at the location where tube segments 26a and 26b meet).

The tube 26 is preferably comprised of flexible portions 52, 54, 56, and 58. Each of the portions can have different size and shape and a mechanical properties. The portions 52, 54, 56, and 58 can be different regions in a one-piece tube, or the portions can be comprised of one or more separate pieces joined together to form tube. By varying the mechanical properties of each flexible segment, such as the Young's modulus (by selection of the material), bending moment of inertia (by altering the cross sectional geometry of the tube), or the length, the properties of the catheter 20 can be adapted to particular catheter functions and/or to facilitate navigating the catheter to a specific location or configuration for a particular function or procedure.

Accordingly, the deflection of the distal end of a flexible portion is governed by the beam bending equation:

$$\epsilon = lmB\sin(\theta - \epsilon)/EI \quad (1)$$

where $\epsilon$ is the tip angular deflection, l is the length of the deflected distal portion of the device, m is the magnetic dipole moment of the magnetic member at the distal end of said flexible portion, $\theta$ is the field orientation angle with respect to the proximal end of the length l, and B is the applied magnetic field. The beam bending equation is useful to illustrate the properties which affect the deflection over even relatively large distances. Accordingly, the bending stiffness (EI/l) and its inverse, the flexibility, of the flexible portions determine the amount by which the distal end of a flexible portion deflects when a magnetic field is applied to the catheter 20. By selecting the material, the cross sectional geometry, and the length of the flexible segments, the deflection of the distal ends of the flexible portions can be adapted to particular catheter functions and/or to facilitate navigating the catheter to a specific location or configuration for a particular function or procedure.

The strength of the applied magnetic field and the magnetic dipole moment of the magnetic member determine the magnetically induced moment that acts on the magnetic member when a magnetic field is applied to the catheter. The magnetic members 42, 44, and 46 transfer the moments to the flexible segments via the mechanical couplings between the flexible segments 52, 54, 56, and 58 and the magnetic members. Thus the selection of the magnetic properties of the magnetic members and the selection of the mechanical properties of the flexible segments also affects how much the distal end of each flexible segment will deflect when the magnetic field is applied to the catheter. Large flexible segment deflections, greater than about 0.1 inch per inch, are desirable because they provide for the smaller turning radii desired for highly navigable catheters 20.

The leads 40 and 44 can contribute to the bending stiffness of the catheter 20 (FIG. 1). Thus, the number, size, and bending stiffness of wires within the lumen 30 should generally be minimized to maximize the flexibility of the flexible segments 140, 142, 144, and 150 although, in other embodiments, the presence of wiring within the lumen 28 may beneficially decrease the flexibility of the flexible segments. While a single, generally round lumen 30 has been shown and described herein, tubes and/or lumens of other shapes, and multiple lumens can be provided to control the flexibility of the catheter and/or to adapt the catheter for particular functions and/or to facilitate navigating the catheter to a specific location or configuration for a particular function or procedure.

Figure 3:
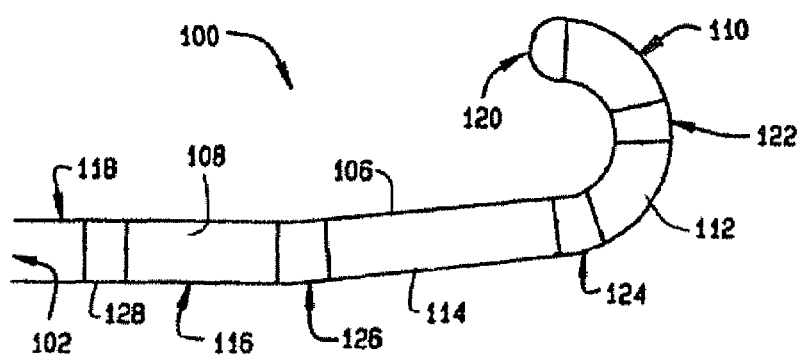
FIG. 3 is a side view of the catheter of Figure a flexed by a magnetic field.

An alternate construction is shown in FIG. 3, such that when a magnetic field is applied to the catheter 20, the catheter bends in an amount and direction depending on the strength of the applied magnetic field, the properties of the magnet elements, and the property of the flexible portions of the tube. The direction of the applied magnetic field is indicated by arrow 40. Upon the application of a magnetic field to the catheter, a magnetically induced moment acts on each magnetic member 46, 48, and 50. These moments tend to turn the magnetic members 46, 48, and 50 in a direction determined by the polarity of the magnet and the direction of the magnetic field. That is, a moment acts on the magnetic members 46, 48, and 50 which tends to orient the magnetic members in the direction of the magnetic field 40. Thus, magnetic members 46, 48, and 50, if unrestrained by the flexible portions 52, 54, 56, and 58 would orient themselves with the applied magnetic field 40. As shown in FIG. 3, the magnetic field 40 turns the magnetic members 46, 48, and 50 in a counterclockwise direction, causing a corresponding counter clockwise flexing of the catheter 20.

The magnitudes of the moments depend on the strength of the applied magnetic field and the magnetic properties of the individual magnetic members 46, 48, and 50. Because the flexible segments 52, 54, 56, and 58 have some finite bending stiffness, equilibrium develops between the magnetically induced moments acting on each magnetic member 46, 48 and 50 and the resisting torques caused by the bending stiffness of the flexible members 52, 54, 56, and 58 Thus, the catheter 20 will flex through a particular angle and stop with the magnetically induced moments in equilibrium with the resisting torques.

A second embodiment of a catheter constructed according to the principles of this invention is indicated generally as 100 in FIG. 3. Catheter 100 has a proximal end 102, a distal 104, and a tubular sidewall 106 having a lumen 108. Catheter 100 could include various electrodes and thermistors described above with respect to catheter 20, but these are omitted in FIG. 3 for clarity. The catheter 100 comprises a plurality of portions of differing flexibility, in accordance with a design to facilitate configuring the catheter with an externally applied magnetic field to assume a desired shape, or to reach a desired location in a subject's body. As shown in FIG. 3, there are at least five portions 110, 112, 114, 116, and 118. These portions can either be different areas of a continuous tube, or they can separate sections formed into a tube. There are also a plurality of magnetically responsive elements, similar to elements 46, 48, and 50. As shown in FIG. 3, there are five elements 120, 122, 124, 126, and 128.

When a magnetic field is applied to the distal end portion of the catheter, the magnetically responsive elements 120, 122, 124, 126 and 128 tend to align their permanent magnetization (or induced magnetization) direction with the direction of the applied field. The flexible portions 110, 112, 114, 116, and 118 apply some resistance to the magnet elements that tends to prevent them from aligning with the applied magnetic field. By providing a plurality of magnetically responsive elements connected by a plurality of flexible portions, the catheter 100 can be designed to assume a particular configuration upon the application of a magnetic field.

When a magnetic field is applied to the distal end portion of the catheter, the magnetically responsive elements 120, 122, 124, 126, and 128 tend to align their permanent magnetically (or induced magnetization) direction with the direction of the applied field. The flexible portions 110, 112, 114, 116, and 118 apply some resistance to the magnet elements that tend to prevent them from aligning with the applied magnetic field, and thereby establishes a lag between the tip direction and the applied field direction. By providing a plurality of magnetically responsive elements connected by a plurality of flexible portion, the catheter 100 can designed to assume a particular configuration upon the application of a magnetic field. The modulus a elasticity (IMB/EI) for each flexible segment is preferably greater than about 0.1, such that the free length of the distal end (of about 0.5 cm) can align within 20 degrees of a magnetic field even where the field is applied in a direction substantially perpendicular to the axial length of the medical device. When the field is applied in a direction substantially perpendicular to the elongate direction of the un-deformed device, the lag (or angle) between tip element and the applied field is less than about 20 degress, and the lag between each successively proximal element and the applied field is less than 35 degrees. The body portion of the medical device applies a torque (ie.—resistance to bending) of no more than about 0.01 N m to resist orientation of the with an applied field.

The magnetic properties of the magnetically responsive elements can also be selected to adapt the catheter to particular functions. For instance, in the preferred embodiment, the magnetization direction of the magnetically responsive elements would preferably be aligned with the axis of the catheter. Aligning the polarity of the magnets enables the catheter to flex through 180 degrees because all of the magnetically induced moments on the magnetic members operate in the same direction. Accordingly, the magnetically induced moments act cumulatively along the length of the catheter, navigating the catheter in an ever tighter curve. Such a reducing radius curve allows the catheter to reach areas in the body, for example the anterior, right, lateral portions of the Mitral Valve, which prior art catheters have difficulty in accessing. By selecting the size and position of the magnets and the stiffness of the flexible portion, the device can extend trans-septally through a puncture in the septal wall of the heart from the right side to the the left side, and touch the anterior right lateral portions of the circumference of the Mitral Valve. Another advantage of a reducing radius catheter over the prior art is that the catheter is softer. Accordingly, pressure which could damage soft tissue is minimized thereby easing patient trauma and improving chances for full patient recovery. It should be noted that this softer, more flexible catheter can also be stiffened by the application of a magnetic field that will cause the magnetic element to remain aligned with the field, and thereby make the catheter's bending resistance four time larger in the presence of the field, as compared to the bending resistance of the catheter in the absence of a field.

In some embodiments the magnetization direction might vary from this arrangement so that the catheter takes on a designed shape upon the application of a magnetic field. It is also possible that although aligned with axis of the catheter, the polarities of adjacent magnets alternate, i.e. so that the north pole of one magnet faces the south pole of an adjacent magnet. By placing the magnetically responsive members in opposition catheters can be constructed which will snake through obstructions, first navigating in one direction, then navigating in the other, and so forth.

Thus the present invention provides a family of highly navigable catheters well suited for reaching areas of the body inaccessible to prior art catheters. The small turning radii available via the invention allow navigation around acute angles and within small, confined chambers within the body. Also, by providing a reducing radius curvature catheter, the invention avoids physician fatigue and internal patient injury induced by the prior art catheters.

While the invention has been described in terms of various specific embodiments, those skilled in the art will recognize that the invention can be practiced with modification within the spirit and scope of the claims.

What is claimed is:

1. A magnetically guidable medical device comprising an elongate body having a proximal end and a distal end; a magnetically responsive tip element at the distal end of the body; and at least one magnetically responsive auxiliary element spaced proximally from the tip element, each of the magnetically responsive elements being separated from the adjacent element by a portion of the body that applies a torque of no more than about 0.01 N-m to resist orientation of the element with an applied magnetic field.

2. The magnetically responsive medical device according to claim 1 wherein all of the magnetically responsive elements are disposed within about 5 cm of the distal tip of the device.

3. The magnetically responsive medical device according to claim 2, wherein there are at least two auxiliary elements, and wherein the distances between adjacent magnetically responsive elements are not all equal.

4. The magnetically responsive medical device according to claim 1 wherein at least one of the at least one auxiliary elements is smaller than the tip element.

5. The magnetically responsive medical device according to claim 1 wherein there are at least two auxiliary elements and wherein the distances between adjacent magnetically responsive elements are not all equal.

6. A magnetically guidable medical device comprising an elongate body having a proximal end and a distal end; a magnetically responsive tip element at the distal end of the body; and at least one magnetically responsive auxiliary element spaced proximally from the tip element, each of the magnetically responsive elements being separated from adjacent elements by flexible portions of the body, the magnetically responsive elements being sized so that, and the flexibility of the portions between the magnetically responsive elements being selected so that the longitudinal axis of the tip element can align within 20 degrees of a magnetic field applied in a direction substantially perpendicular to the elongate axial direction of the undeformed device.

7. The magnetically responsive medical device according to claim 6 wherein all of the magnetically responsive elements are disposed within about 5 cm of the distal tip of the device.

8. The magnetically responsive medical device according to claim 6 wherein the at least one of the at least one auxiliary elements is smaller than the tip element.

9. The magnetically responsive medical device according to claim 6 wherein with a free length of at least about 5 cm the longitudinal axis of the tip element can align within 20 degrees of a magnetic field applied in a direction substantially perpendicular to the elongate direction of the undeformed device.

10. A magnetically guidable medical device comprising an elongate body having a proximal end and a distal end; a magnetically responsive tip element at the distal end of the body; and at least one magnetically responsive element spaced proximally from the tip element, each of the magnetically responsive elements being separated from adjacent elements by flexible portions of the body, wherein (lmB/EI) for each flexible portion is greater than about 0.1, where E is the Young's modulus of the flexible portion, I is the bending moment of inertia of the portion, l is the length of the portion, m is the effective magnetic moment of the magnetically responsive element at the distal end of said flexible portion, and B is the applied magnetic field.

11. The magnetically responsive medical device according to claim 10 wherein all of the magnetically responsive elements are disposed within about 5 cm of the distal tip of the device.

12. The magnetically responsive medical device according to claim 10 wherein at the at least one auxiliary element is smaller than the tip element.

13. The magnetically responsive medical device according to claim 10 wherein there are at least two auxiliary elements and wherein the distances between adjacent magnetically responsive elements are not equal.

14. A magnetically guidable medical device comprising an elongate body having a proximal end and a distal end; a magnetically responsive tip element at the distal end of the body; and at least one magnetically responsive element spaced proximally from the tip element, each of the magnetically responsive elements being separated from adjacent elements by flexible portions of the body, wherein (ImB/EI) for each flexible portion is greater than about 0.1, and less than about 7, where E is the Young's modulus of the flexible portion, I is the bending moment of inertia of the portion, l is the length of the portion, m is the effective magnetic moment of the magnetically responsive element at the distal end of said flexible portion, and B is the applied magnetic field.

15. The magnetically responsive medical device according to claim 14 wherein all of the magnetically responsive elements are disposed within about 5 cm of the distal tip of the device.

16. The magnetically responsive medical device according to claim 14 wherein at least one auxiliary element is smaller than the tip element.

17. The magnetically responsive medical device according to claim 14 wherein there are at least two auxiliary elements and wherein the distance between adjacent magnetically responsive elements differs.

18. A magnetically guidable medical device comprising an elongate body having a proximal end and a distal end; a magnetically responsive tip element at the distal end of the body; and at least one magnetically responsive element spaced proximally from the tip element, each of the magnetically responsive elements being separated from adjacent elements by flexible portions of the body, wherein the lag angle between the tip element and the applied field is less than about 20 degrees, and wherein the lag angle between each successively proximal element and the applied field is less than 35 degrees greater than the lag angle between the next most proximal angle and the applied field, when the field is applied in a direction substantially perpendicular to the elongate direction of the undeformed device.

19. The magnetically responsive medical device according to claim 18 wherein all of the magnetically responsive elements are disposed within about 5 cm of the distal tip of the device.

20. The magnetically responsive medical device according to claim 18 wherein the at least one auxiliary element is smaller than the tip element.

21. The magnetically responsive medical device according to claim 18 wherein there are at least two auxiliary elements, and wherein the distance between adjacent magnetically responsive elements differs.

22. The magnetically responsive medical device according to claim 18 wherein with a free length of at least about 5 cm the longitudinal axis of the tip element can align within 20 degrees of a magnetic field applied in a direction substantially perpendicular to the elongate direction of the undeformed device.

23. A magnetically guidable medical device comprising an elongate body having a proximal end and a distal end; a magnetically responsive tip element at the distal end of the body; and at least one magnetically responsive element spaced proximally from the tip element, each of the magnetically responsive elements being separated from adjacent elements by flexible portions of the body, wherein the magnetically responsive elements are disposed within about 5 cm of the distal tip of the device.

24. The magnetically responsive medical device according to claim 23 wherein the at least one auxiliary element is smaller than the tip element.

25. The magnetically responsive medical device according to claim 23 wherein the distance between adjacent magnetically responsive elements differs.

26. A magnetically guidable medical device comprising an elongate body having a proximal end and a distal end; the device having a distal end portion comprising a magnetically responsive tip element at the distal end of the body; and at least one magnetically responsive element spaced proximally from the tip element, each of the magnetically responsive elements being separated from adjacent elements by flexible portions of the body, the distal portion of the device including the magnets having an effective end-to-end bending stiffness that is at least four times larger in the presence of a magnetic field applied in a direction substantially parallel to the elongate direction of the device than it is in the absence of said applied magnetic field.

27. The magnetically responsive medical device according to claim 26 wherein all of the magnetically responsive elements are disposed within about 5 cm of the distal tip of the device.

28. The magnetically responsive medical device according to claim 26 wherein the at least one auxiliary element is smaller than the tip element.

29. The magnetically responsive medical device according to claim 26 wherein the distance between adjacent magnetically responsive elements varies.

30. The magnetically responsive medical device according to claim 26 wherein the effective end-to-end bending stiffness that is at least four times larger in the presence of a magnetic field of at least 0.08 Tesla than it is in the absence of said applied magnetic field.

31. A magnetically guidable medical device comprising an elongate body having a proximal end and a distal end; the device having a distal end portion comprising a magnetically responsive tip element at the distal end of the body; and at least one magnetically responsive element spaced proximally from the tip element, each of the magnetically responsive elements being separated from adjacent elements by flexible portions of the body, the size and position of the magnets and the stiffness of the flexible portions being selected so that when the device extends trans-septally through a puncture in the septal wall of the heart from right side to left side, it can touch the anterior right lateral portions of the circumference of the Mitral Valve.

32. The magnetically responsive medical device according to claim 31 wherein all of the magnetically responsive elements are disposed within about 5 cm of the distal tip of the device.

33. The magnetically responsive medical device according to claim 32 wherein the at least one auxiliary element is smaller than the tip element.

34. The magnetically responsive medical device according to claim 31 wherein there are at lest two auxiliary element and wherein the distance between adjacent magnetically responsive elements varies.

35. The magnetically responsive medical device according to claim 31 wherein the device extends trans-septally through a puncture in the septal wall of the heart from right side to left side, it can touch the anterior right lateral portions of the circumference of the Mitral Valve, with a maximum applied field of 0.08 Tesla.

36. A magnetically guidable medical device comprising an elongate body having a proximal end and a distal end; the device having a distal end portion comprising a magnetically responsive tip element at the distal end of the body; and at least one magnetically responsive element spaced proximally from the tip element, each of the magnetically responsive elements being separated from adjacent elements by flexible portions of the body, the size and position of the magnets and the stiffness of the flexible portions being selected so that the distal end of the device can bend at least 180 degrees over a length of less than about 5 cm, wherein the distance between adjacent magnetically responsive elements varies.

37. A magnetically guidable medical device comprising an elongate body having a proximal end and a distal end; the device having a distal end portion comprising a magnetically responsive tip element at the distal end of the body; and at least one magnetically responsive element spaced proximally from the tip element, each of the magnetically responsive elements being separated from adjacent elements by flexible portions of the body, the size and position of the magnets and the stiffness of the flexible portions being selected so that the distal end of the device can bend at least 180 degrees over a length of less than about 5 cm, wherein the distal end of the device can bend at least 180 degrees over a length of less than about 5 cm with an applied magnetic field of at least about 0.08 Tesla.

* * * * *

UNITED STATES PATENT AND TRADEMARK OFFICE
CERTIFICATE OF CORRECTION

PATENT NO.        : 7,346,379 B2                                              Page 1 of 1
APPLICATION NO.   : 11/319039
DATED             : December 27, 2005
INVENTOR(S)       : Michael J. Eng et al.

It is certified that error appears in the above-identified patent and that said Letters Patent is hereby corrected as shown below:

In Col. 1, line 30, delete "of this invention",
In Col. 3, line 40, replace "FIG. 2" with "FIG. 1",
In Col. 3, line 43, replace "42'" with "52'",
In Col. 3, line 46, replace "46'" with "52'",
In Col. 3, line 50, replace "46'" with "52'",
In Col. 3, line 53, replace "46'" with "52'",
In Col. 3, line 67, replace "46'" with "52'",
In Col. 4, line 2, replace "46'" with "52'",
In Col. 4, line 4, replace "46'" with "52'",
In Col. 4, line 7, replace "42', 42", and 42''''" with "52', 52", 52''''",
In Col. 4, line 10, replace "42'" with "52'",
In Col. 4, line 23, delete "52",
In Col. 4, line 24, delete "52",
In Col. 4, line 61, replace "42, 44, and 46" with "46, 48 and 50",
In Col. 4, line 63, delete "52",
In Col. 5, line 9, replace "140, 142, 144 and 150" with "110, 112, 114 and 116",
In Col. 5, line 25, replace "40" with "60",
In Col. 5, line 34, delete "52",
In Col. 5, line 42, delete "52",
In Col. 5, line 46, delete "52",
In Col. 6, line 17, replace "magnetically" with "magnetization".

Signed and Sealed this

Seventh Day of July, 2009

JOHN DOLL
*Acting Director of the United States Patent and Trademark Office*